(12) United States Patent
Robinson (10) Patent No.: US 8,475,478 B2
(45) Date of Patent: Jul. 2, 2013

(54) CLEANING APPARATUS AND METHOD FOR HIGH-SPEED ROTATIONAL ATHERECTOMY DEVICES

(75) Inventor: Paul J. Robinson, Mahtomedi, MN (US)

(73) Assignee: Cardiovascular Systems, inc., St. Paul, MN (US)

( * ) Notice: Subject to any disclaimer, the term of this patent is extended or adjusted under 35 U.S.C. 154(b) by 123 days.

(21) Appl. No.: 11/773,517

(22) Filed: Jul. 5, 2007

(65) Prior Publication Data

US 2009/0012548 A1 Jan. 8, 2009

(51) Int. Cl.
*A61B 17/22* (2006.01)

(52) U.S. Cl.
USPC .......................................................... 606/159

(58) Field of Classification Search
USPC ............... 606/159, 1, 68, 180, 168, 170, 167, 606/108
See application file for complete search history.

(56) References Cited

U.S. PATENT DOCUMENTS

| | | | |
|---|---|---|---|
| 3,137,975 A | 6/1964 | Jones et al. | |
| 3,557,496 A | 1/1971 | Martin | |
| 5,030,201 A | 7/1991 | Palestrant | |
| 5,047,040 A | 9/1991 | Simpson et al. | |
| 5,160,318 A * | 11/1992 | Shuler | 604/22 |
| 5,217,474 A * | 6/1993 | Zacca et al. | 606/159 |
| 5,297,310 A | 3/1994 | Cox et al. | |
| 5,391,152 A | 2/1995 | Patterson | |
| 5,456,681 A | 10/1995 | Hajjar | |
| 5,512,044 A * | 4/1996 | Duer | 604/22 |
| 5,695,507 A * | 12/1997 | Auth et al. | 606/159 |
| 5,702,413 A | 12/1997 | Lafontaine | |
| 6,045,623 A | 4/2000 | Cannon | |
| 6,053,923 A * | 4/2000 | Veca et al. | 606/80 |
| 6,146,395 A * | 11/2000 | Kanz et al. | 606/159 |
| 6,454,779 B1 | 9/2002 | Taylor | |
| 6,494,890 B1 | 12/2002 | Shturman et al. | |
| 6,497,711 B1 * | 12/2002 | Plaia et al. | 606/159 |
| 6,505,631 B2 | 1/2003 | Fischer et al. | |
| 6,579,298 B1 * | 6/2003 | Bruneau et al. | 606/159 |
| 6,638,288 B1 | 10/2003 | Shturman et al. | |
| 6,945,977 B2 * | 9/2005 | Demarais et al. | 606/128 |
| 2002/0007190 A1 * | 1/2002 | Wulfman et al. | 606/167 |
| 2002/0095170 A1 * | 7/2002 | Krolik et al. | 606/200 |
| 2003/0004537 A1 * | 1/2003 | Boyle et al. | 606/200 |
| 2004/0082962 A1 | 4/2004 | Demarais et al. | |
| 2004/0158270 A1 | 8/2004 | Wyzgala et al. | |
| 2004/0181251 A1 * | 9/2004 | Hacker et al. | 606/170 |

FOREIGN PATENT DOCUMENTS

| | | |
|---|---|---|
| JP | 57-59526 | 4/1982 |
| JP | 8-509390 | 10/1996 |
| JP | 2002-506668 | 3/2002 |
| WO | WO 97/03618 | 2/1997 |

\* cited by examiner

*Primary Examiner* — Thomas McEvoy
(74) *Attorney, Agent, or Firm* — Winthrop & Weinstine, P.A.

(57) ABSTRACT

Apparatus and method for maximizing efficiency of tissue removal from body passageways is provided. A rotational atherectomy device comprises, inter alia, an elongated, flexible and rotatable drive shaft with an enlarged cutting surface disposed thereon, guide wire and catheter. The distal end of catheter may have a cutting surface cleaner, either attached thereto or integrated therein. The cleaner may be outwardly radially flexible and biased against the drive shaft. The cleaner may be opened to accommodate the enlarged cutting surface for cleaning particles trapped therein as a consequence of abrading as it is either advanced distally over the drive shaft and/or the drive shaft is retracted proximally toward the cleaner to accommodate the diameter of the enlarged cutting section. The cleaner comprises an inner surface having an abrasive surface for mechanically scraping and dislodging material trapped in the enlarged cutting head tissue removing surface.

7 Claims, 7 Drawing Sheets

CLEANING APPARATUS AND METHOD FOR HIGH-SPEED ROTATIONAL ATHERECTOMY DEVICES

BACKGROUND OF THE INVENTION

1. Field of the Invention

The invention generally relates to devices and methods for maximizing efficiency of tissue removal from body passageways, such as removal of atherosclerotic plaque from arteries, utilizing a high-speed rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a burr covered with an abrasive cutting material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it.

U.S. Pat. No. 5,314,438 (Shturman) discloses another atherectomy device having a drive shaft with a section of the drive shaft having an enlarged diameter, at least a segment of this enlarged cutting head being covered with an abrasive material to define an abrasive segment of the drive shaft. When rotated at high speeds, the abrasive segment is capable of removing stenotic tissue from an artery.

U.S. Pat. No. 6,494,890 (Shturman) discloses an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation.

Each of these prior art devices comprise an abrasive cutting surface in some form in certain embodiments. Each of these abrasive cutting surfaces may become plugged or filled with various types of non-abraidable material as the abrasive cutting surface cuts through lesions. When this occurs, the cutting efficiency of the abrasive cutting surface is diminished. Thus, it would be highly desirable to clear the abrasive cutting surface of the material adhered to or otherwise stuck to the abrasive cutting surface.

BRIEF SUMMARY OF THE INVENTION

Apparatus and method for maximizing efficiency of tissue removal from body passageways is provided. A rotational atherectomy device comprises, inter alia, an elongated, flexible and rotatable drive shaft with an enlarged cutting surface disposed thereon, guide wire and catheter. The distal end of catheter may have a cutting surface cleaner, either attached thereto or integrated therein. The cleaner may be outwardly radially flexible and biased against the drive shaft. The cleaner may be opened to accommodate the enlarged cutting surface for cleaning particles trapped therein as a consequence of abrading as it is either advanced distally over the drive shaft and/or the drive shaft is retracted proximally toward the cleaner to accommodate the diameter of the enlarged cutting section. The cleaner comprises an inner surface having an abrasive surface for mechanically scraping and dislodging material trapped in the enlarged cutting head tissue removing surface.

Advantageously, certain embodiments of the present invention provide an apparatus and method for dislodging material in the cuffing surface of atherectomy devices.

Another object of the invention is to provide an apparatus and method for improving the efficiency of tissue removal from body passageways, e.g., stenosis from arteries.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Figure 1:
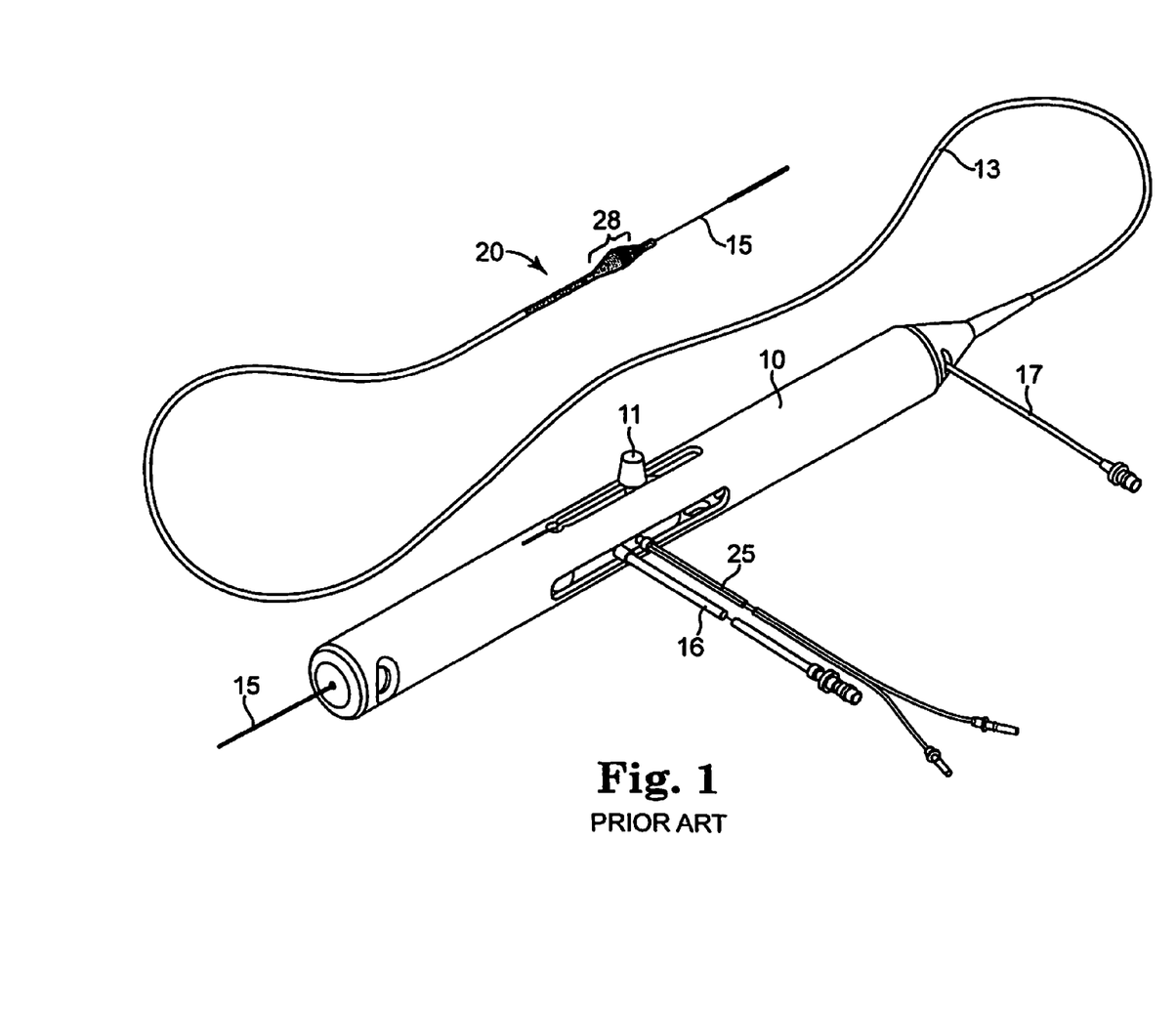
FIG. 1 is a perspective view of one embodiment of a prior art high-speed rotational atherectomy device.

FIG. 1 illustrates a typical and exemplary rotational atherectomy device that may utilize the present invention. Such a device is generally described in U.S. Pat. No. 5,314,438 (Shturman) and U.S. Pat. No. 6,494,890 (Shturman), the disclosures of each incorporated herein by reference in their entirety.

The exemplary rotational atherectomy device of FIG. 1 includes a handle portion 10, an elongated, flexible drive shaft 20, an enlarged cutting section 28, and an elongated catheter 13 extending distally from the handle portion 10. Enlarged cutting section 28 is shown as a solid piece attached to the drive shaft 20 for exemplary purposes. This form of cutting section 28 and others will be discussed further herein. The drive shaft 20 and enlarged cutting section 28 are constructed from helically coiled wire. The catheter 13 has a distal end and a lumen in which most of the length of the drive shaft 20 is disposed, except for its enlarged cutting section 28 and a short section distal to the enlarged cutting section 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. The handle 10 also desirably includes a control knob 11 for advancing and retracting the turbine and drive shaft 20 with respect to the catheter 13 and the body of the handle.

Figure 2:
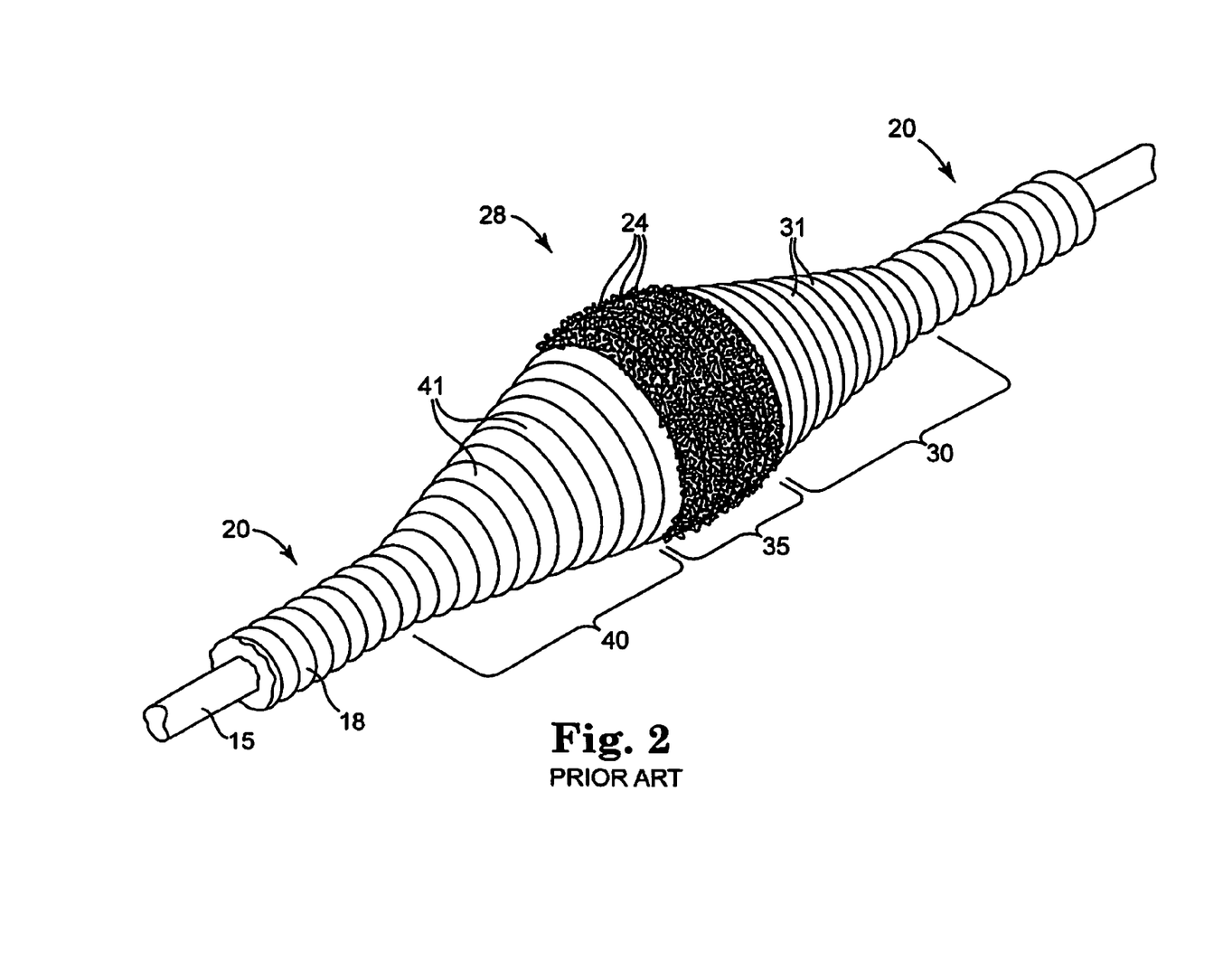
FIG. 2 is a perspective broken-away view of a prior art cutting head used with high-speed rotational atherectomy devices.
Figure 3:
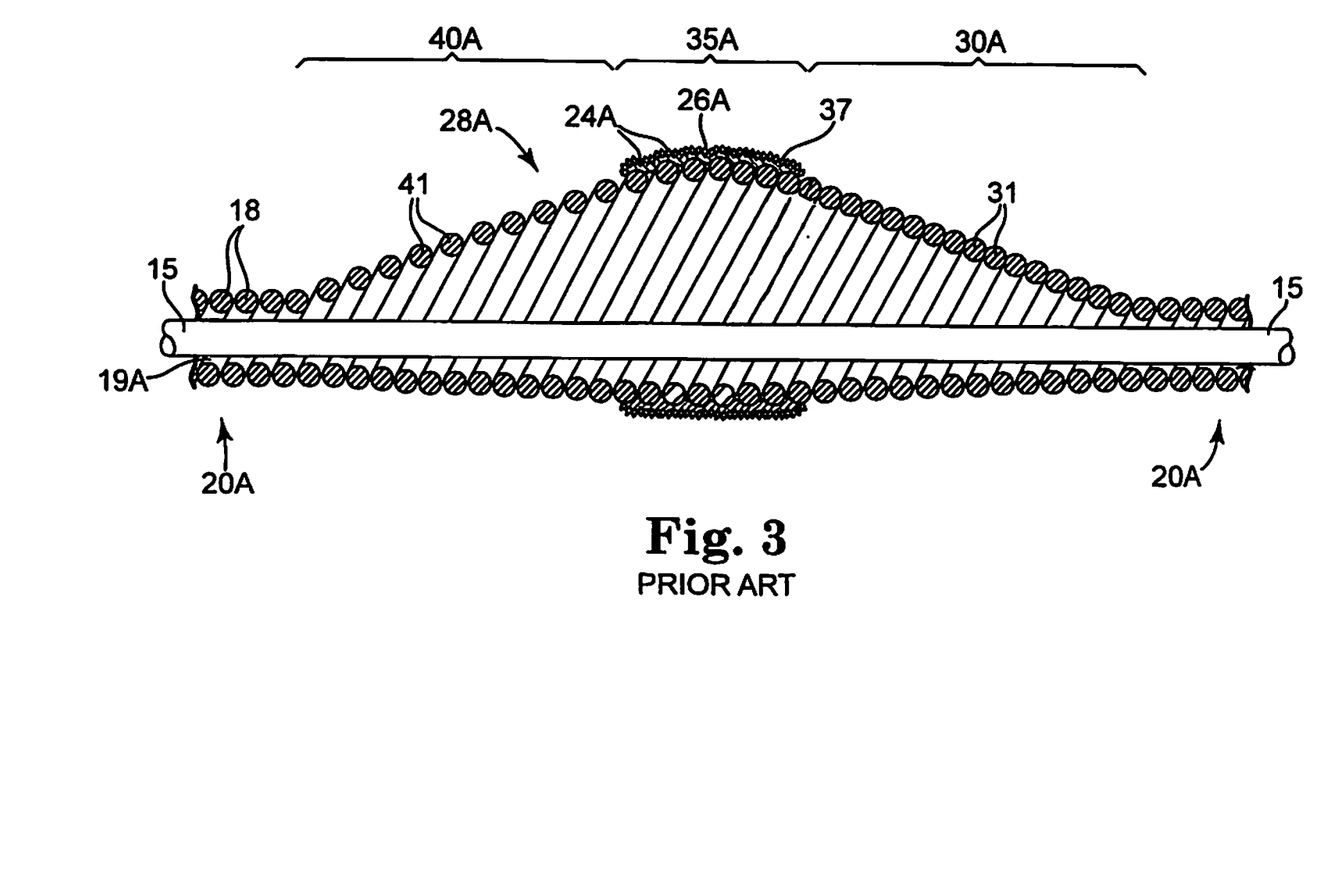
FIG. 3 is a broken-away, longitudinal cross-sectional broken-away view of a prior art eccentric cutting head formed from the drive shaft and used with high-speed rotational atherectomy devices.
Figure 4:
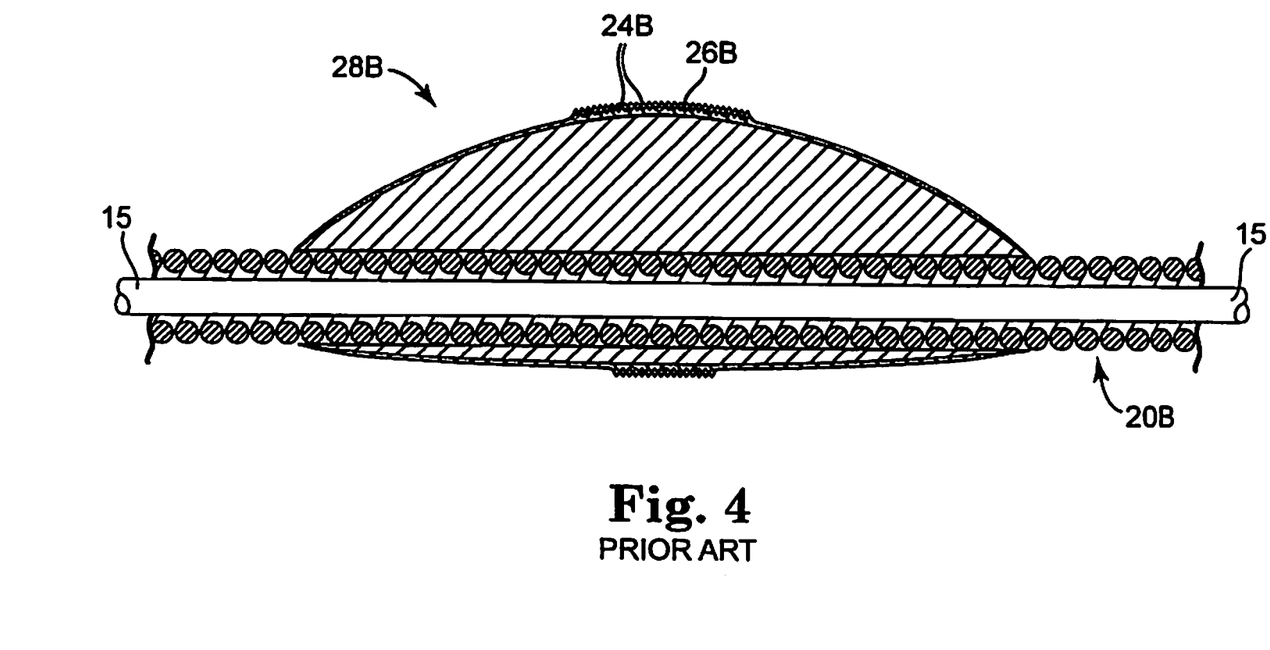
FIG. 4 is a longitudinal cross-sectional broken-away view of a prior art solid eccentric abrasive burr attached to a drive shaft used with low-speed rotational atherectomy devices.

FIGS. 2-4 illustrate details of prior art enlarged cutting sections in FIG. 1. FIG. 2 thus provides an enlarged and substantially concentric cutting section, used for high-speed rotational atherectomy procedures, that comprises a concentric enlarged diameter section of a drive shaft 28. The enlarged diameter section 28 includes proximal 30, intermediate 35 and distal 40 portions. The eccentric enlarged diameter section 28 further includes an external surface capable of removing tissue. A tissue removing surface 37 comprising a coating of an abrasive material 24 to define a tissue removing segment of the drive shaft 20 is shown attached directly to the wire turns of the drive shaft 20 by a suitable binder 26. The drive shaft 20 is comprised of one or more helically wound wires 18 which define a guide wire lumen 19 and a hollow cavity 25 within the enlarged cutting head 28. This form of enlarged cutting section embodied by the concentric enlarged diameter section of the drive shaft 28 is disclosed generally in U.S. Pat. No. 5,314,438 to Shturman.

Turning to FIG. 3, a cutaway cross-sectional view of another prior art form of enlarged cutting section used for high-speed rotational atherectomy procedures is provided. Here, the eccentric enlarged diameter section 28A, rotated over guide wire 15, of the drive shaft 20 includes, as above, proximal 30A, intermediate 35A and distal 40A portions. The eccentric enlarged diameter section 28A further includes an external abrasive surface capable of removing tissue. A tissue removing surface 37 comprising a coating of an abrasive material 24A to define a tissue removing segment of the drive shaft 20 is shown attached directly to the wire turns of the drive shaft 20A by a suitable binder 26A. Wire turns 31 of the proximal portion 30A of the eccentric enlarged diameter section 28A preferably have diameters that progressively increase distally at a generally constant rate, thereby forming generally the shape of a cone, thus forming proximal and distal conical portions. Wire turns 41 of the distal portion 40A preferably have diameters that progressively decrease distally at a generally constant rate, thereby forming generally the shape of a cone. The profile of the intermediate portion 35 comprises gradually changing diameters to provide a generally convex outer surface which is shaped to provide a smooth transition between proximal and distal conical portions of the enlarged eccentric diameter section 28A of the drive shaft 20. Thus, this prior art enlarged cutting section presents an eccentric profile. Such an eccentric enlarged cutting section 28A is disclosed generally in, e.g., U.S. Pat. No. 6,494,890 to Shturman.

Turning now to FIG. 4, another prior art approach to the enlarged cutting section is provided. This solution employs a solid asymmetrical abrasive burr 28B attached to a flexible drive shaft 20B, rotated over a guide wire 15 at low speeds such as provided by U.S. Pat. No. 5,681,336 to Clement, the disclosure of which is hereby incorporated by reference in its entirety. The eccentric tissue removing burr 28B has a coating of abrasive particles 24B secured to a portion of its outer surface by a suitable binding material 26B.

Figure 5:
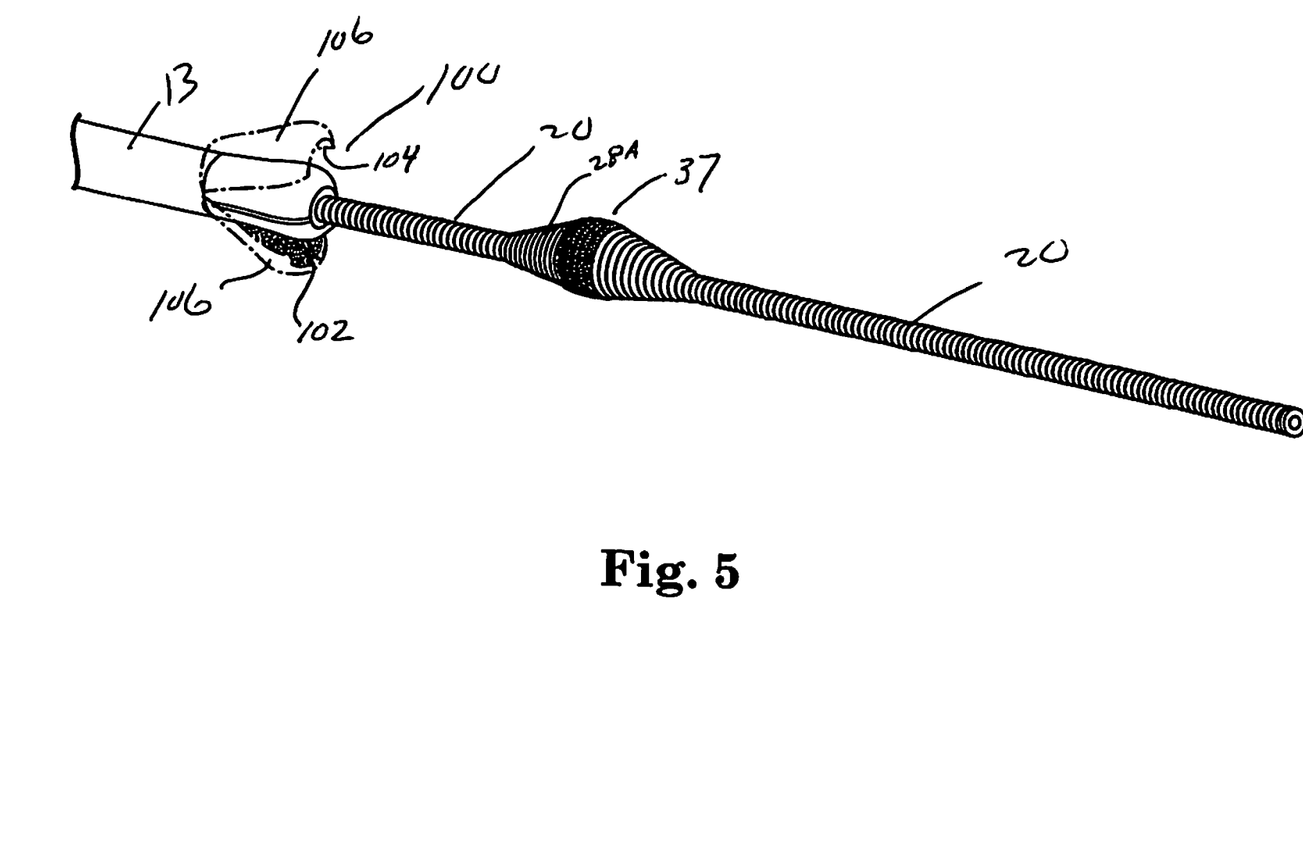
FIG. 5 is a perspective view of one embodiment of the cleaning apparatus cutting of the present invention.

Returning now to FIG. 1 in combination with FIG. 5, the catheter 13 has a lumen in which most of the length of the drive shaft 20 may be typically disposed, except for its enlarged cutting section 28 and a short section distal to the enlarged cutting section 28. The drive shaft 20 also contains an inner lumen 19, permitting the drive shaft 20 to be advanced and rotated over a guide wire 15.

As illustrated in FIG. 5, distal end of catheter 13 may have a distal cutting surface cleaner 100, either attached thereto or integrated therein. Cleaner 100 may be outwardly radially flexible and biased against the drive shaft 20. The cleaner 100 may open sufficiently as it is either advanced distally over the drive shaft 20 or the drive shaft 20 is retracted proximally toward the cleaner 100 to accommodate the diameter of the enlarged cutting section 28. The cleaner 100 comprises an inner surface which further comprises an abrasive surface 102 thereon that may clean and remove material caught in the enlarged cutting head tissue removing surface 37. The cleaner 100 may thus dislodge particles trapped within the tissue removing surface 37 by simply longitudinally passing the tissue removing surface 37 through the cleaner 100 and allowing the cleaner's abrasive surface 102 to scrape the material away.

Alternatively, the tissue removing surface 37 may be moved into the cleaner 100 and then the drive shaft 20 rotated to provide additional force to dislodge particles trapped within the tissue removing surface 37.

The embodiment of cleaner 100 in FIG. 5 comprises two openable sections 106, with a biasing force generally holding the two openable sections 106 compressed against each other.

Openable sections 106 may be comprised of a rigid material or a semi-flexible material. Mechanisms for providing the radially inward biasing forces for the openable sections 106 of the present invention are well known to those skilled in the art. As the enlarged diameter section 28A presses against the openable sections 106, forcing the radially flexible openable sections 106 to accommodate the enlarged diameter section 28A and engage the tissue removing surface 37 with the cleaner's abrasive surface 102 disposed on the inner surface 104 of each openable section 106. The openable sections 106 are illustrated in an opened position in phantom in FIG. 5. Those skilled in the art will recognize that other equivalent embodiments for the cleaner 100 may exist, including inter alia, more than two (upper and lower) openable sections 106. For example, two or more openable sections 106, i.e., three or four or a plurality of openable sections 106 may be used. The radially inward biasing forces of the openable sections 106 of cleaner 100 provide, in combination with the longitudinal motion of the tissue removing surface 37 relative to the cleaner's abrasive surface 104, and/or rotational movement of the drive shaft 20, sufficient force to scrape and dislodge particles trapped within the tissue removing surface 37.

The Figures illustrate enlarged eccentric diameter section 28A of the drive shaft 20, whereon the tissue removing surface 37 is disposed, however, the present invention is certainly not restricted to this illustrative embodiment of an enlarged cutting surface or enlarged cutting head. Those skilled in the art will recognize that alternate high-speed rotational atherectomy cutting surfaces or cutting heads may be cleaned according to the present invention. Additionally, those skilled in the art will recognize that low-speed rotational cutting surfaces or cutting heads may be cleaned according to the present invention. Further, the enlarged cutting surface may be eccentric or concentric. The enlarged cutting surface may be formed from the wire turns of the drive shaft or may be an abrasive burr mounted thereon. The cleaning of each such enlarged cutting surface and/or cutting head is within the scope of the present invention.

Thus, cutting surface is defined herein to comprise high-speed or low-speed rotational atherectomy cutting heads having abrasive surfaces. Cutting surface is further defined to comprise enlarged diameter sections formed from the wire turns of a rotational atherectomy drive shaft, wherein the enlarged diameter section may be concentric or eccentric, such as the embodiment of the present invention illustrated herein. Cutting surface is further defined to comprise solid, semi-solid or hollow cutting heads and/or burrs having abrasive surfaces and that are attached or mounted to a rotational atherectomy drive shaft.

Saline solution, introduced into catheter 13, and thus cleaner 100, by the fluid supply line 17 shown in FIG. 1 may be used to flush the cutting surface 28A when the cutting surface 28A is within the openable sections 106. The saline flush of the cutting surface 28A may occur any time after the cutting surface 28A has pressed or urged the openable sections 106 open and before, during and/or after the cutting method described herein. In this manner, the abrasive cutting surface 28A may be cleaned during the treatment. Thus, it is not necessary to remove the abrasive cutting surface 28A from the patient to clean it.

Figure 6:
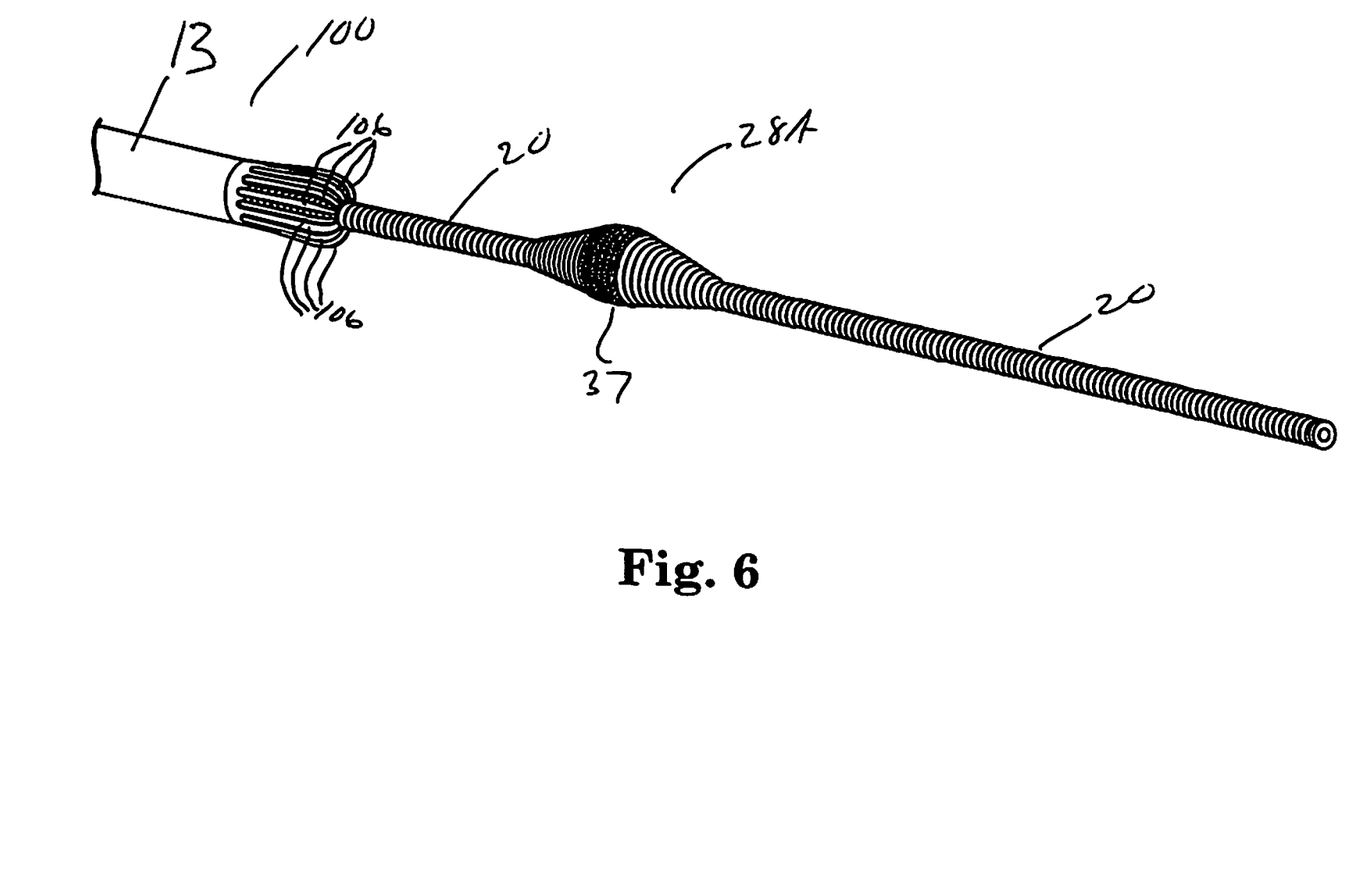
FIG. 6 is a perspective view of one embodiment of the cleaning apparatus cutting of the present invention.

Turning now to FIG. 6, an alternate embodiment of the cleaner 100 is provided. In this embodiment, a plurality of openable sections 106 are provided, each openable section 106 separated by a gap 110 from the next adjacent openable section 106. This configuration provides enhanced flexibility for the openable sections 106. Those skilled in the art will recognize that the gap 110 between adjacent openable sections 106 may be smaller than shown or not required. In other words, an alternate embodiment may comprise adjacent openable sections 106 configured with little or no gapping 110 therebetween.

The cleaner of FIG. 6 functions as described above in connection with FIG. 5, with the exception that there are more openable sections 106 with a gap 110 therebetween. Thus, as the enlarged diameter section 28A presses against the cleaner, the openable sections 106 widen and open to accommodate the enlarged diameter section. Abrasive surface 102 on the interior of each openable section 104, as described in connection with FIG. 5, provides for the dislodging of material trapped on the abrasive tissue removing surface 37 of the enlarged diameter section 28A. This dislodging process may be achieved by proximal and/or distal longitudinal movement of the tissue removing surface 37 relative to the cleaner 100. Alternatively, rotation of the drive shaft 20, thus rotating the tissue removing surface 37 within the cleaner 100 may be used either alone, or in conjunction with longitudinal movement of the tissue removing surface 37 relative to the cleaner 100.

Figure 7:
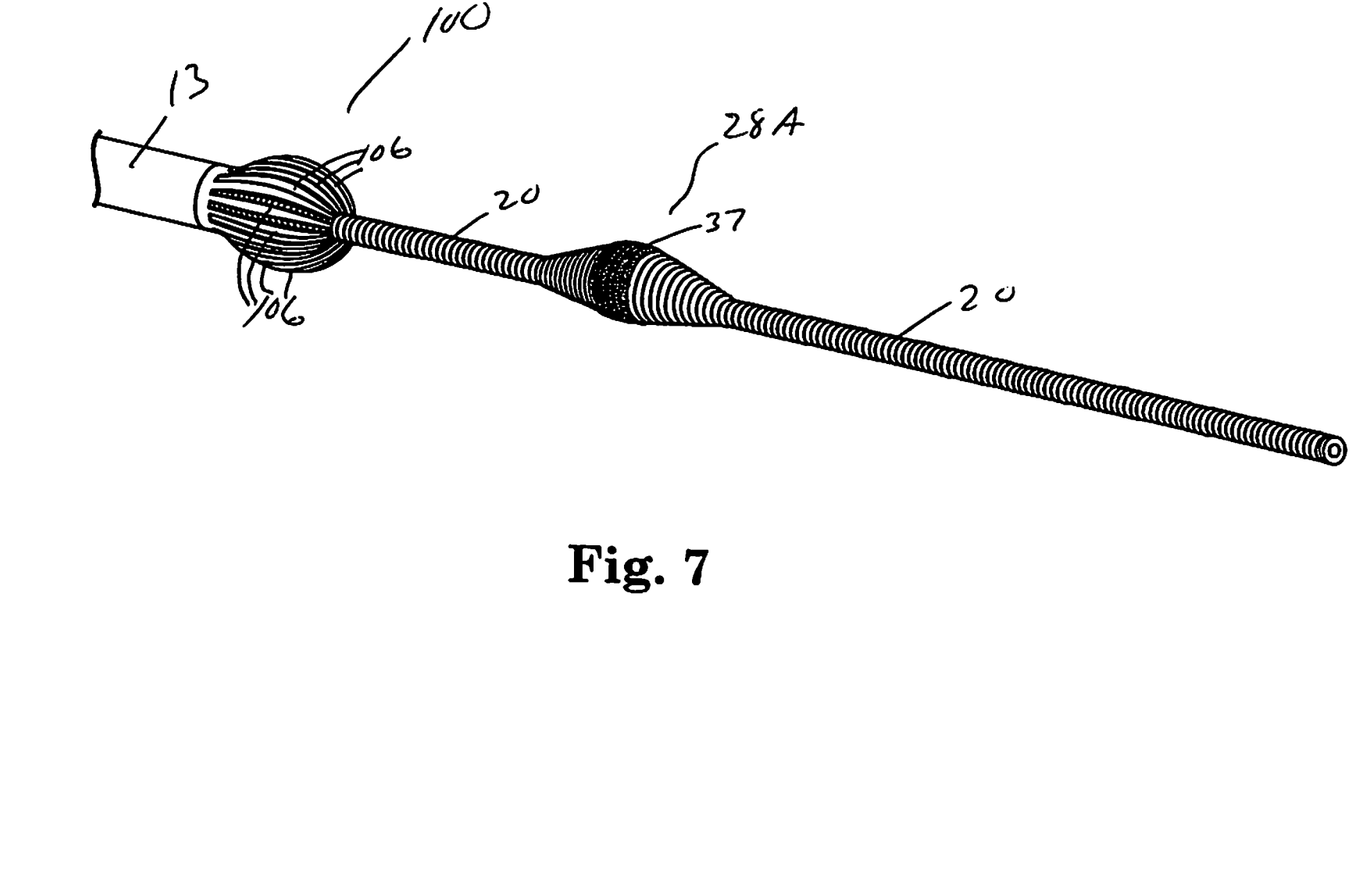
FIG. 7 is a perspective view of one embodiment of the cleaning apparatus cutting of the present invention.

The openable sections of FIGS. 5 and 6 illustrate openable sections 106 that comprise a diameter roughly the same as that of catheter 13 prior to the introduction of the enlarged cutting head 28A therein. FIG. 7 illustrates a slightly different embodiment wherein the openable sections 106 are formed with a diameter that is larger than that of the catheter 13. This may provide for additional biasing force by the openable sections 106 against the tissue removing surface 37 as the surface 37 is scraped against the abrasive surfaces on the inner portion of the openable sections.

A method according to the present invention for maximizing efficiency of tissue removal from body passageways, may comprise providing a cutting surface on an elongated flexible drive shaft; providing a cleaner on a the distal end of an elongated catheter; positioning an elongated catheter and the elongated flexible drive shaft within the elongated catheter's lumen within a body passageway and adjacent a stenosis; rotating the elongated flexible drive shaft within the body passageway to abrade the stenosis with the cutting surface; retracting the elongated flexible drive shaft proximally away from the stenosis and toward the catheter's cleaner; opening the cleaner and inserting the cutting surface; scrapingly engaging the cutting surface with the cleaner's abrasive surface to remove any material lodged in the cutting surface; and resuming abrading of the stenosis.

Additional method steps may include rotating the drive shaft to enhance the scraping cleaning process and/or longitudinally moving the catheter and/or drive shaft so that the cleaner longitudinally scrapes the cutting surface and/or flushing the cutting surface with saline.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A rotational atherectomy device for cleaning stenotic material from an enlarged cutting surface after abrading a stenosis within a body passageway, comprising:
   a guide wire;
   an elongate, flexible catheter comprising a lumen, a distal end and a distal cutting surface cleaner disposed on the distal end; and an elongate and flexible drive shaft comprising an enlarged cutting surface and an inner lumen, the drive shaft capable of advancement, retraction and rotation over the guide wire and at least a portion of the drive shaft capable of advancement, retraction and rotation within the lumen of the catheter, wherein the distal cutting surface cleaner further comprises a plurality of openable sections, wherein the plurality of openable sections are disposed adjacent each other with a gap therebetween when the enlarged cutting surface is completely deployed distal to the distal cutting surface cleaner, the gaps extending completely through the distal cutting surface cleaner, and wherein each of the plurality of openable sections comprising inner abrasive surfaces and being outwardly radially flexible and biased radially inward, wherein the plurality of openable sections are biasingly held in a closed position by a biasing force and wherein the enlarged cutting surface is movable to be at least partially accommodated within the distal cutting surface cleaner, thereby overcoming the biasing force and causing the plurality of openable sections to move to an open position and wherein the enlarged cutting surface is scrapingly engaged by the inner abrasive surfaces to clean the stenotic material therefrom.

2. The rotational atherectomy device of claim 1 wherein the distal cutting surface cleaner is attached to the distal end of the catheter.

3. The rotational atherectomy device of claim 1, wherein the distal cutting surface cleaner is integrated into the distal end of the catheter.

4. The rotational atherectomy device of claim 1, wherein the plurality of openable sections further comprise an inner surface, the inner surface comprising an abrasive.

5. The rotational atherectomy device of claim 1, wherein the enlarged cutting surface is concentric with the drive shaft.

6. The rotational atherectomy device of claim 1, wherein the enlarged cutting surface is eccentric with the drive shaft.

7. The rotational atherectomy device of claim 1, wherein the enlarged cutting surface is mounted onto the drive shaft.

* * * * *